US012653953B2

(12) United States Patent (10) Patent No.: US 12,653,953 B2

Auld et al. (45) Date of Patent: Jun. 16, 2026

(54) EXTERNALLY POWERED SYRINGE DRIVERS AND SYSTEMS AND METHODS FOR USING THEM

(71) Applicant: ALTAVIZ, LLC, Irvine, CA (US)

(72) Inventors: Jack R. Auld, Laguna Niguel, CA (US); Matthew McCawley, San Clemente, CA (US); John C. Dunne, Jr., Costa Mesa, CA (US)

(73) Assignee: ALTAVIZ, LLC, Irvine, CA (US)

( * ) Notice: Subject to any disclaimer, the term of this patent is extended or adjusted under 35 U.S.C. 154(b) by 237 days.

(21) Appl. No.: 17/670,441

(22) Filed: Feb. 12, 2022

(65) Prior Publication Data

US 2022/0257863 A1 Aug. 18, 2022

Related U.S. Application Data

(60) Provisional application No. 63/149,204, filed on Feb. 12, 2021.

(51) Int. Cl.
A61M 5/155 (2006.01)
A61M 5/20 (2006.01)
(Continued)

(52) U.S. Cl.
CPC .......... A61M 5/2053 (2013.01); A61M 5/155 (2013.01); *A61F 9/00727* (2013.01);
(Continued)

(58) Field of Classification Search
CPC ............ A61M 5/14526; A61M 5/1551; A61M 2005/2086
See application file for complete search history.

(56) References Cited

U.S. PATENT DOCUMENTS 3,768,472 A 10/1973 Hodosh et al.
4,561,856 A 12/1985 Cochran
(Continued)

FOREIGN PATENT DOCUMENTS

EP 1302185 A1 4/2003

OTHER PUBLICATIONS

Korean Intellectual Property Office, International Search Report for corresponding International Application No. PCT/US2022/016245 (ALTA-0220 WO), May 31, 2023, 3 pages.
(Continued)

*Primary Examiner* — Emily L Schmidt
(74) *Attorney, Agent, or Firm* — William A. English; Vista IP Law Group LLP

(57) ABSTRACT

Syringe drivers and injector devices are provided. The driver includes a housing including a port communicating with a gas chamber therein and connectable to an external air source, and a cavity that receives a syringe containing an agent. A drive piston within the housing includes a first end disposed adjacent the gas chamber and a second end including a plunger connectable to the syringe. A damping mechanism is provided within that housing that is coupled to the drive piston that includes a damper piston within a damping fluid chamber such that, when the drive piston is advanced by gas delivered into the gas chamber from the external source to deliver the agent from the syringe, damping fluid within the damping fluid chamber flows through an orifice or valve from a first region to the second region, thereby limiting movement of the drive piston.

24 Claims, 6 Drawing Sheets

(51) Int. Cl.

| | | |
|---|---|---|
| *A61F 9/007* | (2006.01) | |
| *A61M 5/145* | (2006.01) | |
| *A61M 5/31* | (2006.01) | |

(52) U.S. Cl.

CPC . *A61M 5/14526* (2013.01); *A61M 2005/2086* (2013.01); *A61M 2005/3128* (2013.01)

(56) References Cited

U.S. PATENT DOCUMENTS

| | | | |
|---|---|---|---|
| 4,744,786 A * | 5/1988 | Hooven | A61M 5/155 |
| | | | 604/246 |
| 5,019,037 A * | 5/1991 | Wang | A61F 9/00727 |
| | | | 604/23 |
| 7,901,377 B1 | 3/2011 | Harrison et al. | |
| 10,716,892 B2 | 7/2020 | Flowers | |
| 11,071,824 B2 | 7/2021 | Auld | |

| | | | |
|---|---|---|---|
| 2002/0165483 A1 * | 11/2002 | Miller | A61M 35/003 |
| | | | 604/82 |
| 2007/0221796 A1 * | 9/2007 | Silverman | A61M 5/1415 |
| | | | 248/161 |
| 2017/0182253 A1 | 6/2017 | Folk et al. | |

OTHER PUBLICATIONS

Korean Intellectual Property Office, Written Opinion for corresponding International Application No. PCT/ US2022/016245 (ALTA-0220 WO), May 31, 2023, 6 pages.

European Patent Office, Response Filed for EP Patent Application No. 22753474.0, Aug. 21, 2025, 24 pages.

European Patent Office, Extended European Search Report for EP Patent Application No. 22753474.0, Nov. 18, 2024, 10 pages.

European Patent Office, Examination Report for EP Application No. 22 753 474.0-1122, Dec. 12, 2025, 7 pages.

* cited by examiner

EXTERNALLY POWERED SYRINGE DRIVERS AND SYSTEMS AND METHODS FOR USING THEM

RELATED APPLICATION DATA

The present application claims benefit of U.S. provisional application Ser. No. 63/149,204, filed Feb. 12, 2021, the entire disclosure of which is expressly incorporated by reference herein.

TECHNICAL FIELD

The present application relates to devices and methods for delivering agents into a patient's body and, more particularly, to syringe drivers and injector devices for use with external air sources, and systems and methods for using such drivers.

BACKGROUND

There are many applications involving delivery of a medicament or other agent into a patient's body. For example, injectors are often used to deliver viscous fluids into a patient's eye, e.g., oil tamponades during retinal detachment surgery. Such injectors may be connected to an external air source, e.g., a surgical console, such as the Constellation® system manufactured by Alcon. Such consoles may have a variable air pressure source, e.g., providing pressure between about 0-80 psi, that may be foot-pedal controlled by the surgeon during use.

For example, a syringe containing highly viscous silicone oil tamponade, e.g., having a viscosity between about 1000-5000 cP, may be connected to the air pressure line of the console and then inserted into a patient's eye to deliver the oil into the posterior region of the eye. The syringe may be introduced into the eye through a 23 g or 25 g trocar cannula, and then air pressure from the console may be used to advance the syringe plunger to deliver the oil. Because of the high viscosity of the oil, the limited pressure available from the console, and the relatively small diameter of the delivery cannula, flow of the oil may be limited by the restriction due to the cannula.

When such systems are used to deliver low viscosity agents, however, e.g., having viscosities of about one centipoise (1 cP) or less, variations in syringe plunger friction, variations in downstream cannula size, and/or flow resistance and other variations in tissue resistance may result in variable resistance and/or unpredictable delivery rates when the syringe is driven by a high pressure external air source.

Therefore, improved devices and methods for delivering agents into a patient's body would be useful.

SUMMARY

The present application is directed to devices and methods for delivering agents into a patient's body and, more particularly, to syringe drivers and injector devices for use with external air sources, and systems and methods for using such drivers.

In accordance with one example, a syringe driver is provided for use with an external air source that includes a housing comprising a port communicating with a gas chamber within the housing and connectable to the external air source, and a cavity sized to receive a syringe containing an agent; a drive piston comprising a first end disposed adjacent the gas chamber and a second end comprising a plunger connectable to the syringe received within the cavity, the drive piston movable from an initial first position to a second position when gas is delivered from the air source into the gas chamber, thereby advancing the plunger to deliver the agent from the syringe; and a damping fluid chamber including a damper piston disposed therein between a first region filled with damping fluid and a second region of the damping fluid chamber and one or more passages, valves, and the like communicating between the first region and the second region such that movement of the drive piston between the first and second positions causes the damping fluid to flow through the one or more passages or valves from the first region to the second region, thereby limiting movement of the drive piston.

In accordance with another example, a syringe driver is provided that includes a housing comprising a proximal end including a port communicating with a gas chamber within the housing and connectable to the external air source, and a distal end including a cavity sized to receive a syringe containing an agent; a drive piston comprising a first end disposed adjacent the gas chamber and a second end comprising a plunger connectable to the syringe received within the cavity, the drive piston movable from an initial proximal position to a distal position when gas is delivered from the air source into the gas chamber, thereby advancing the plunger to deliver the agent from the syringe; and a damping fluid chamber including a damper piston disposed therein between a first region filled with damping fluid and a second region of the damping fluid chamber and one or more passages, valves, and the like communicating between the first region and the second region such that movement of the drive piston between the proximal and distal positions causes the damping fluid to flow through the one or more passages or valves from the first region to the second region, thereby limiting movement of the drive piston.

In accordance with still another example, an injector device is provided that includes a housing comprising a proximal end including a port communicating with a gas chamber within the housing and connectable to the external air source, and a distal end; an agent chamber within the distal end including an agent piston and an outlet port extending from the distal end; a drive piston comprising a first end disposed adjacent the gas chamber and a second end comprising a plunger connected to the agent piston, the drive piston movable from an initial proximal position to a distal position when gas is delivered from the air source into the gas chamber, thereby advancing the plunger and agent piston to deliver the agent from the from the agent chamber through the outlet port; and a damping fluid chamber including a damper piston disposed therein between a first region filled with damping fluid and a second region of the damping fluid chamber and one or more passages, valves, and the like communicating between the first region and the second region such that movement of the drive piston between the proximal and distal positions causes the damping fluid to flow through the one or more passages or valves from the first region to the second region, thereby limiting movement of the drive piston.

In accordance with yet another example, an injector device is provided for use with an external air source that includes a housing comprising a proximal end including a port communicating with a gas chamber within the housing and connectable to the external air source, and a distal end; an agent chamber within the distal end including an agent piston and an outlet port extending from the distal end; a drive piston comprising a first end disposed adjacent the gas chamber and a second end comprising a plunger connected to the agent piston, the drive piston movable from an initial proximal position to a distal position when gas is delivered from the air source into the gas chamber, thereby advancing the plunger and agent piston to deliver the agent from the from the agent chamber through the outlet port; a damping fluid chamber within the drive piston; and a damper piston mounted on a shaft axially fixed relative to the housing and disposed within the damping fluid chamber between a first region filled with damping fluid and a second region of the damping fluid chamber, and one or more passages in the damper piston communicating between the first region and the second region such that movement of the drive piston between the first and second positions causes the damping fluid to flow through the one or more passages from the first region to the second region, thereby limiting movement of the drive piston.

In accordance with still another example, a system is provided for performing an injection that includes an injector device comprising a housing comprising a proximal end including a port communicating with a gas chamber within the housing and connectable to the external air source, and a distal end; an agent chamber within the distal end including an agent piston and an outlet port extending from the distal end; a drive piston comprising a first end disposed adjacent the gas chamber and a second end comprising a plunger connected to the agent piston, the drive piston movable from an initial proximal position to a distal position when gas is delivered from the air source into the gas chamber, thereby advancing the plunger and agent piston to deliver the agent from the from the agent chamber through the outlet port; a damping fluid chamber within the drive piston; and a damper piston mounted on a shaft axially fixed relative to the housing and disposed within the damping fluid chamber between a first region filled with damping fluid and a second region of the damping fluid chamber, and one or more passages in the damper piston communicating between the first region and the second region such that movement of the drive piston between the first and second positions causes the damping fluid to flow through the one or more passages from the first region to the second region, thereby limiting movement of the drive piston; and a source of pressurized gas connectable to the port.

In accordance with yet another example, a method is provided for performing an injection that includes providing a syringe driver including a housing comprising a proximal end including a port communicating with a gas chamber within the housing, a distal end, a drive piston, and a damping mechanism including a damping fluid chamber including a damper piston disposed therein between a first region filled with damping fluid and a second region of the damping fluid chamber and one or more passages, valves, and the like communicating between the first region and the second region; inserting a syringe containing one or more agents into a cavity of the housing such that an agent piston of the syringe is coupled to a drive piston within the housing and an outlet port of the syringe is disposed adjacent the distal end; connecting an external air source to the port; connecting a cannula to the outlet port; introducing the cannula into a patient's body; and activating the external air source such that the drive piston moves from an initial first position to a second position, thereby advancing the plunger to deliver the agent from the syringe and, wherein movement of the drive piston between the first and second positions causes the damping fluid to flow through the one or more passages or valves from the first region to the second region, thereby limiting movement of the drive piston.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

DETAILED DESCRIPTION

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Figure 1A:
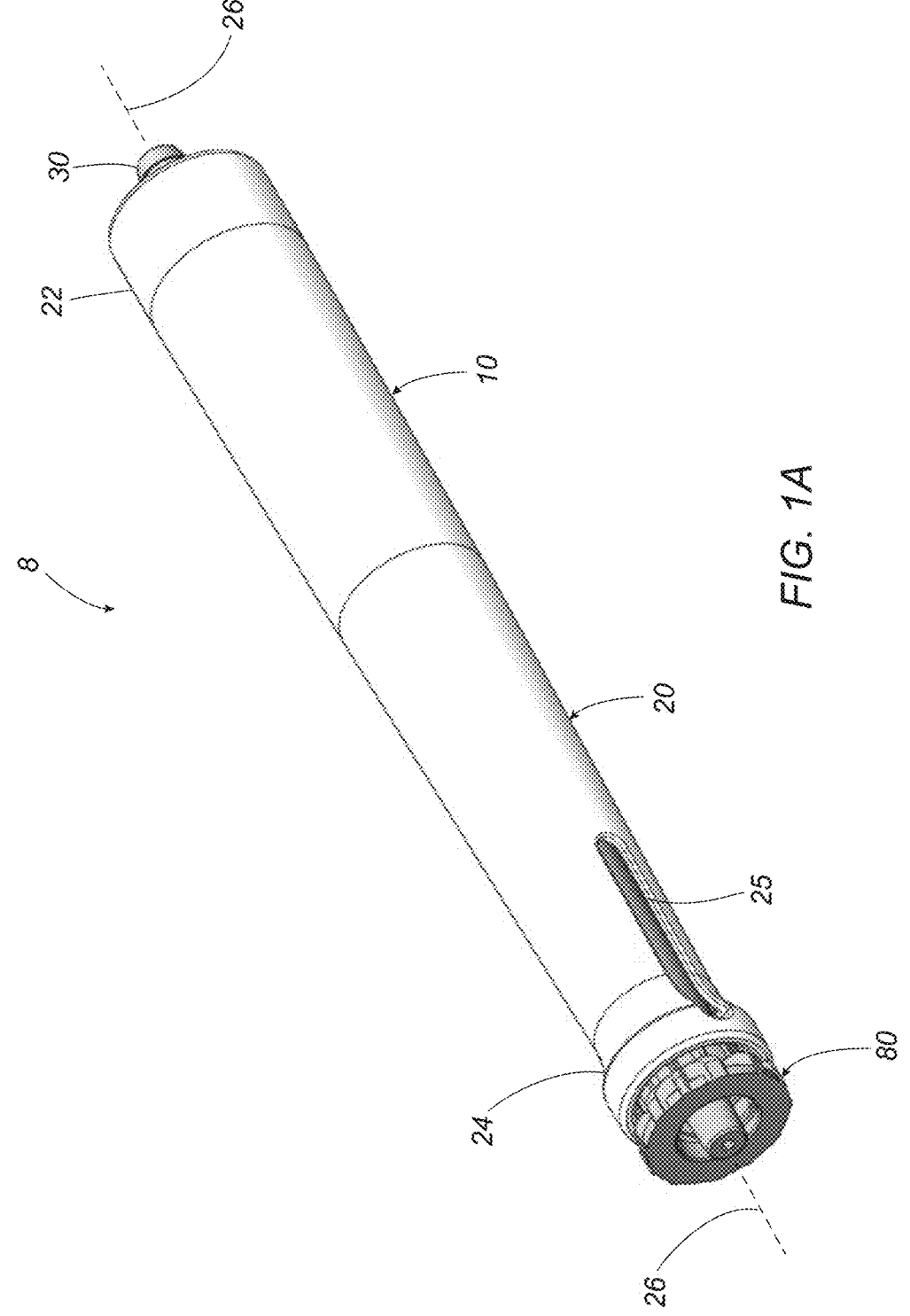
FIG. 1A is a perspective view of an example of a syringe driver.
Figures 1B, 1C:
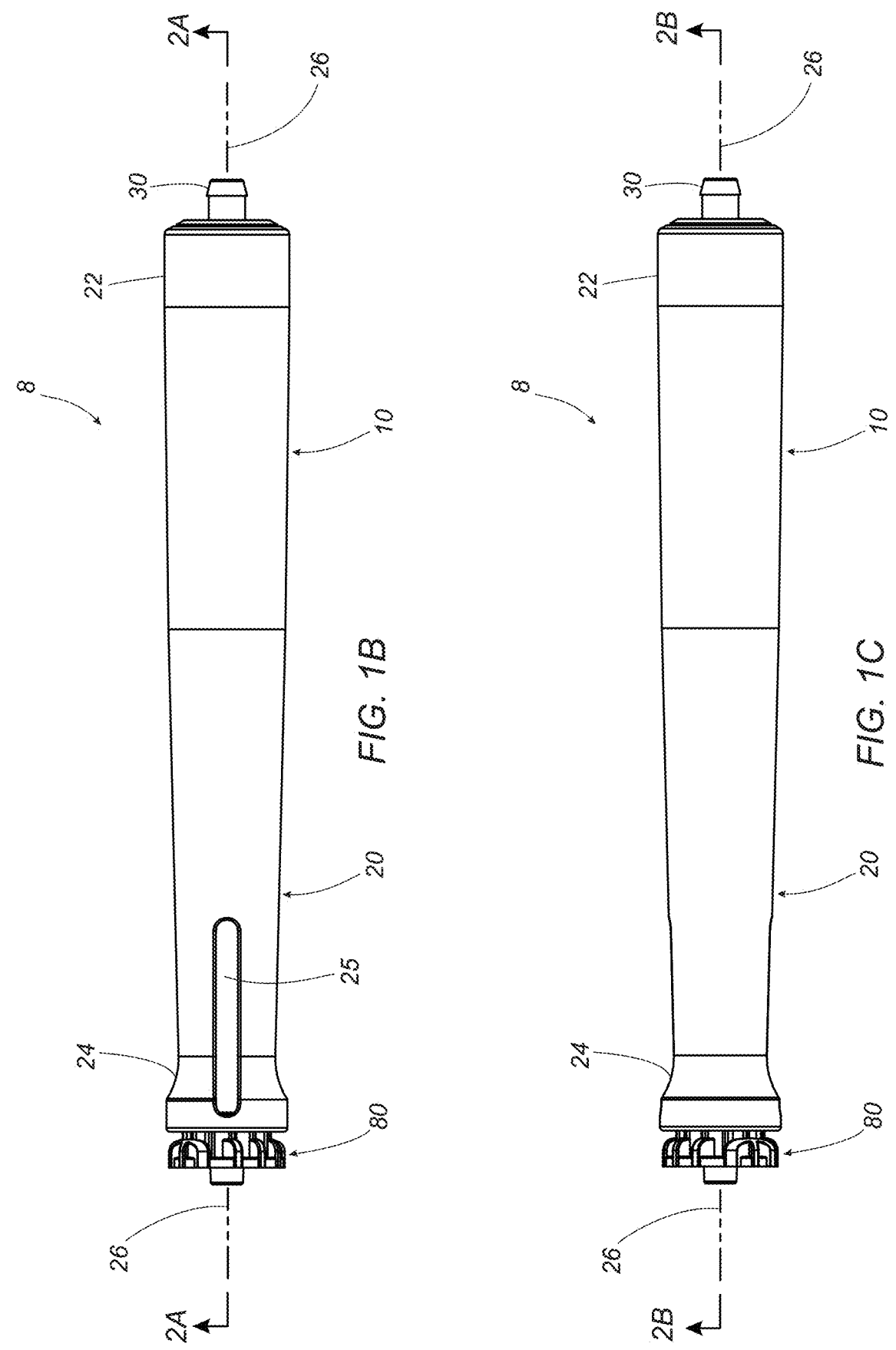
FIGS. 1B and 1C are side views of the syringe driver of FIG. 1A.

Turning to the drawings, FIGS. 1A-1C show an example of an injector device 8 that includes a syringe driver 10 for use with an external air source (not shown) and a syringe or other container 80 containing one or more agents, e.g., for delivery into a patient's eye or another location within the patient's body. As described further elsewhere herein, a syringe 80 may be loaded into the syringe driver 10, which may be connected to an external air source, such as a surgical console (not shown), which may be actuated to deliver the agent into a patient's body. For example, the devices, systems, and methods herein may be used for controlled delivery of therapies into the back of a patient's eye, such as subretinal tissue plasminogen activators, subretinal gene therapies, retinal adhesives, and the like. Such procedures may involve delivering relatively low viscosity agents, e.g., fluids having a viscosity of one centipoise (1 cP) or less, and/or agents having a variable viscosity (e.g., in the case of retinal adhesives). Due to the low viscosity of such fluids, the overall flow rate using conventional injectors may be highly variable and/or unpredictable. The devices, systems, and methods herein may provide damping that provides the primary resistance to the flow of the agent being delivered, e.g., resulting in a throttling action that provides an upper, safe limit to the flow rate of the agent and/or allowing for exquisite control of the delivery flow rate, as described elsewhere herein. Alternatively, the injector devices herein may be used for other applications, e.g., during retinal detachment surgery, to deliver silicone oil tamponade or other highly viscous material, e.g., having a viscosity between about 1000-5000 cP, into the posterior region of a patient's eye, as described elsewhere herein.

Figures 2A, 2B:
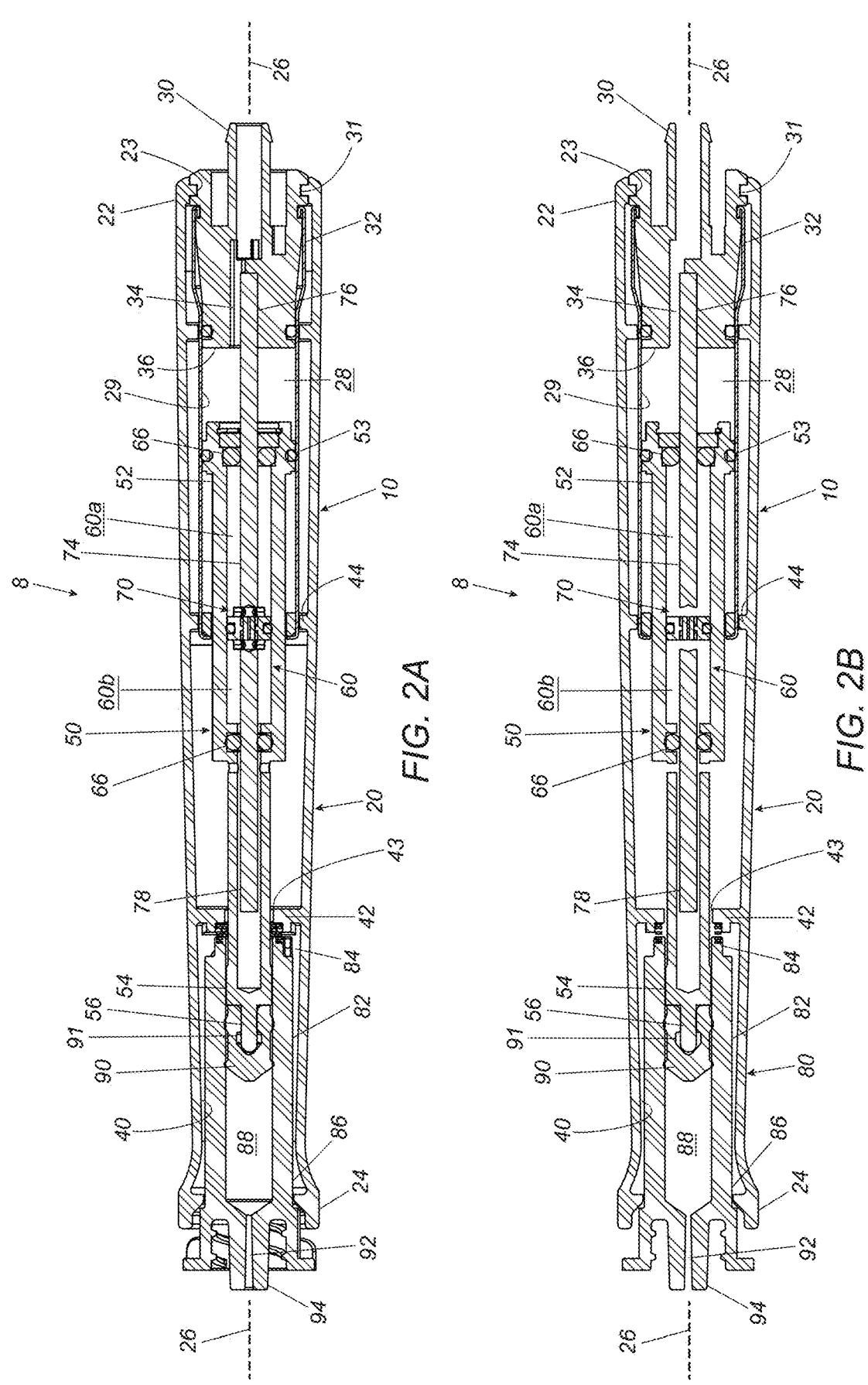
FIGS. 2A and 2B are cross-sectional views of the syringe driver of FIGS. 1A-1C.

With additional reference to FIGS. 2A and 2B, the syringe driver 10 includes a housing 20 including a proximal end 22 and a distal end 24 defining a longitudinal axis 26 therebetween, and one or more chambers or cavities therein. For example, as shown, the housing 20 may be an elongate tubular body including one or more internal partitions or other structures to support its internal components. The housing may be formed using conventional materials and materials, e.g., formed from plastic, metal, and/or composite materials. The housing 20 may have a size, e.g., diameter and/or length to accommodate manipulation of the injector device 8, optionally, including texturing and/or other features (not shown) to facilitate holding and/or otherwise manipulating the injector device 8 during use.

The housing 20 may include a port 30 on the proximal end 22 connectable to an external air source (not shown) that communicates with a gas chamber 28 within the housing 20. For example, as shown, a plug 32 may be inserted into and/or otherwise attached to the proximal end 22 of the housing 20 that includes the port 30 and a gas inlet passage 34 extending from the port 30 to a distal end 36 of the plug 32, which may define a proximal wall of the gas chamber 28. The gas chamber 28 may include a tubular inner wall 29 mounted within the housing 20 or, alternatively, the gas chamber 28 wall may be formed directly in and/or be defined by surfaces of the housing 20 itself.

The proximal end 22 of the housing 20 and the plug 32 may include cooperating connectors to secure the plug within the proximal end 22. For example, as shown, the proximal end 22 may include an annular ridge 23 and the plug 32 may include a corresponding recess 31 into which the ridge 23 may be received to permanently (or optionally removably) attach the plug 32 to the housing 20. In addition or alternatively, the plug 32 may be attached to the housing 20 using one or more of bonding with adhesives, fusing, welding, and the like. Alternatively, the port 30 and gas inlet passage 34 may be integrally formed in the housing 20, e.g., by molding or otherwise integrally forming an end wall including the port 30 on the proximal end 22.

The port 30 may include one or more connectors that allow an external air source, e.g., tubing communicating with a surgical console (not shown), to be connected to the port 30 to provide pressurized air or other compressible gas to operate the syringe driver 10, as described elsewhere herein. For example, as shown in FIGS. 1B-2B, the port 30 may include a male nipple, e.g., which may be inserted into an end of tubing, thereby providing a substantially airtight interference fit. Alternatively, a Luer fitting, one or more threads, and/or other connector may be provided on the port 30 and/or tubing from the air source (not shown) to provide a desired connection.

As shown in FIGS. 2A and 2B, the housing 20 also includes a cavity 40 adjacent the distal end 24 sized to receive a syringe 80 or other container for one or more agents intended for delivery into a patient's body. As shown, the housing 20 may include an interior partition 42 offset proximally from the distal end 24 a distance sufficient to allow insertion of the syringe 80, e.g., to limit insertion of the syringe 80 into the housing 20.

In the example shown, the syringe 80 includes a barrel 82 including a proximal end 84, a substantially closed distal end 86, and an agent chamber 88 for containing the agent. A syringe piston 90 is slidably disposed in the proximal end 84 that may be coupled to the syringe driver 10, as described elsewhere herein, such that the agent may be delivered through an outlet 92 in the distal end 86. The distal end 86 may include an outlet port 94, e.g., including a Luer fitting and/or other connector, to which a needle or other tubular cannula (not shown) may be connected to deliver the agent. Alternatively, a needle or other cannula may be permanently attached to and/or integrated into the distal end 86 of the barrel 82. In another alternative, the syringe 80 may be integrated into the housing of the syringe driver, e.g., by forming an agent chamber directly in the driver housing and forming or attaching an outlet port on the distal end of the housing (not shown).

The housing 20 and/or syringe 80 may include one or more connectors for securing the syringe 80 once received in the cavity 40, e.g., to allow the syringe 80 to be removably or permanently received in the cavity 40. For example, one or more detents, threads, and the like (not shown) may be provided on the syringe 80 and housing 20, e.g., on the internal partition 42 and proximal end 84 of the syringe 80 and/or inside the distal end 24 of the housing 20 and on the distal end 86 of the barrel 80. For example, a desired syringe 80 may be selected and simply inserted into the cavity 40, whereupon the connectors may automatically secure the syringe 80 and ready the injector device 8 for use.

Optionally, as shown in FIGS. 1A and 1B, the housing 20 may include one or more windows or other transparent surfaces, e.g., window 25, to allow a user to visually observe the syringe 80 within the cavity 40, e.g., to monitor flow of the agent from the injector device 8 during delivery.

With continued reference to FIGS. 2A and 2B, a drive piston 50 is provided within the housing 20 that includes a first or proximal end 52 disposed adjacent the gas chamber 28 and a second or distal end 54 including a plunger 56 connectable to the agent piston 90 of the syringe 80 received within the cavity 40. In the example shown, the internal partition 42 includes a passage 43 therethrough through which the second end 54 of the driver piston 50 is slidably received to provide the plunger 56 within the syringe cavity 40. As shown, the agent piston 90 may include a recess 91 into which the plunger 56 may be received when the syringe 80 is inserted into the cavity 40 such that subsequent distal movement of the drive piston 50 causes corresponding distal movement to the agent piston 90. In addition or alternatively, the plunger 56 and/or agent piston 90 may include one or more connectors to further couple them together, e.g., one or more detents, threads, and the like (not shown) that permanently or removably connect the piston 90 the plunger 56.

Figures 3, 3A:
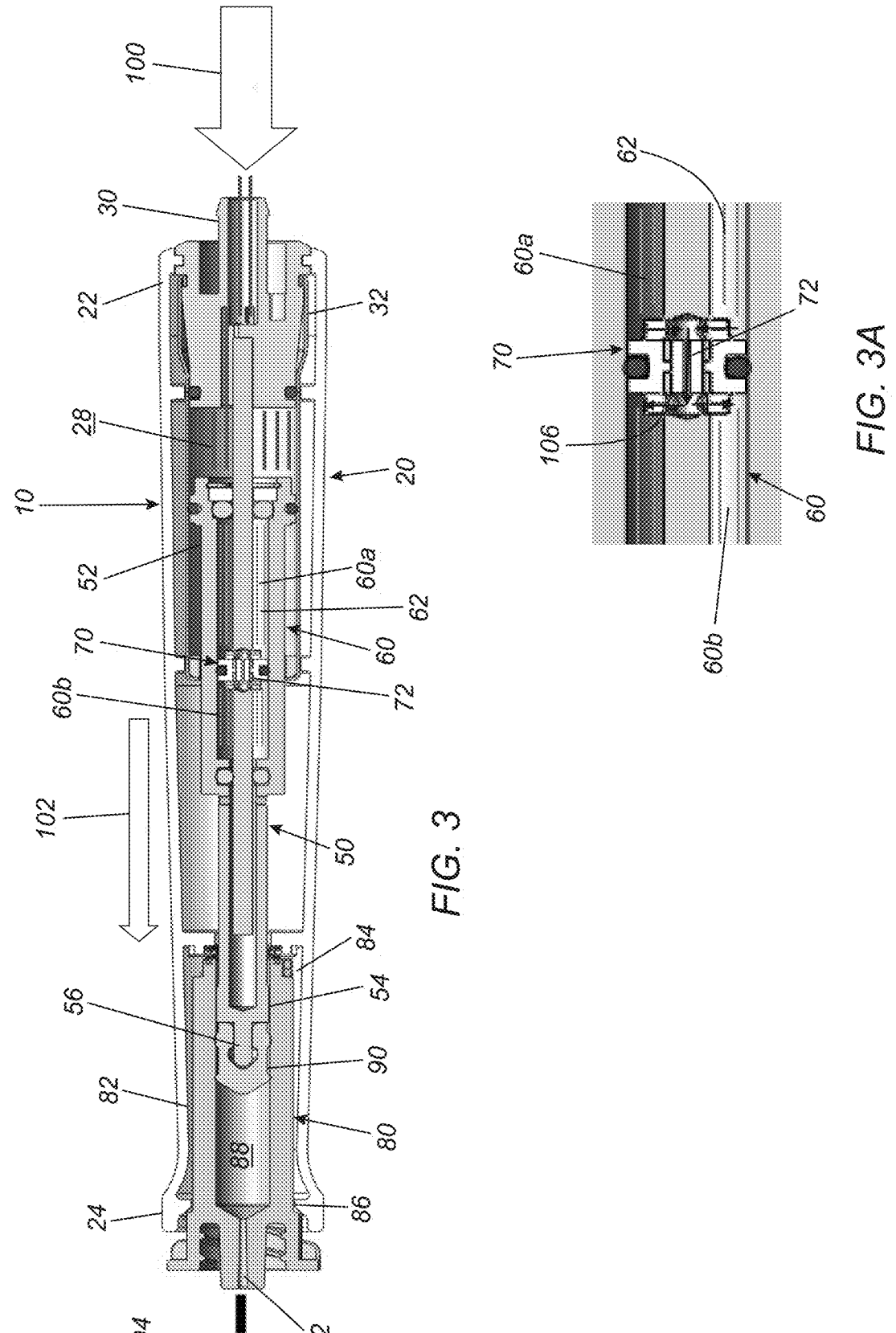
FIG. 3 is a cross-sectional view of the syringe driver of FIGS. 1A-1C showing operation when the driver is powered by an external air source.
FIG. 3A is a detail showing a damper piston of the syringe driver of FIG. 3.
Figure 4:
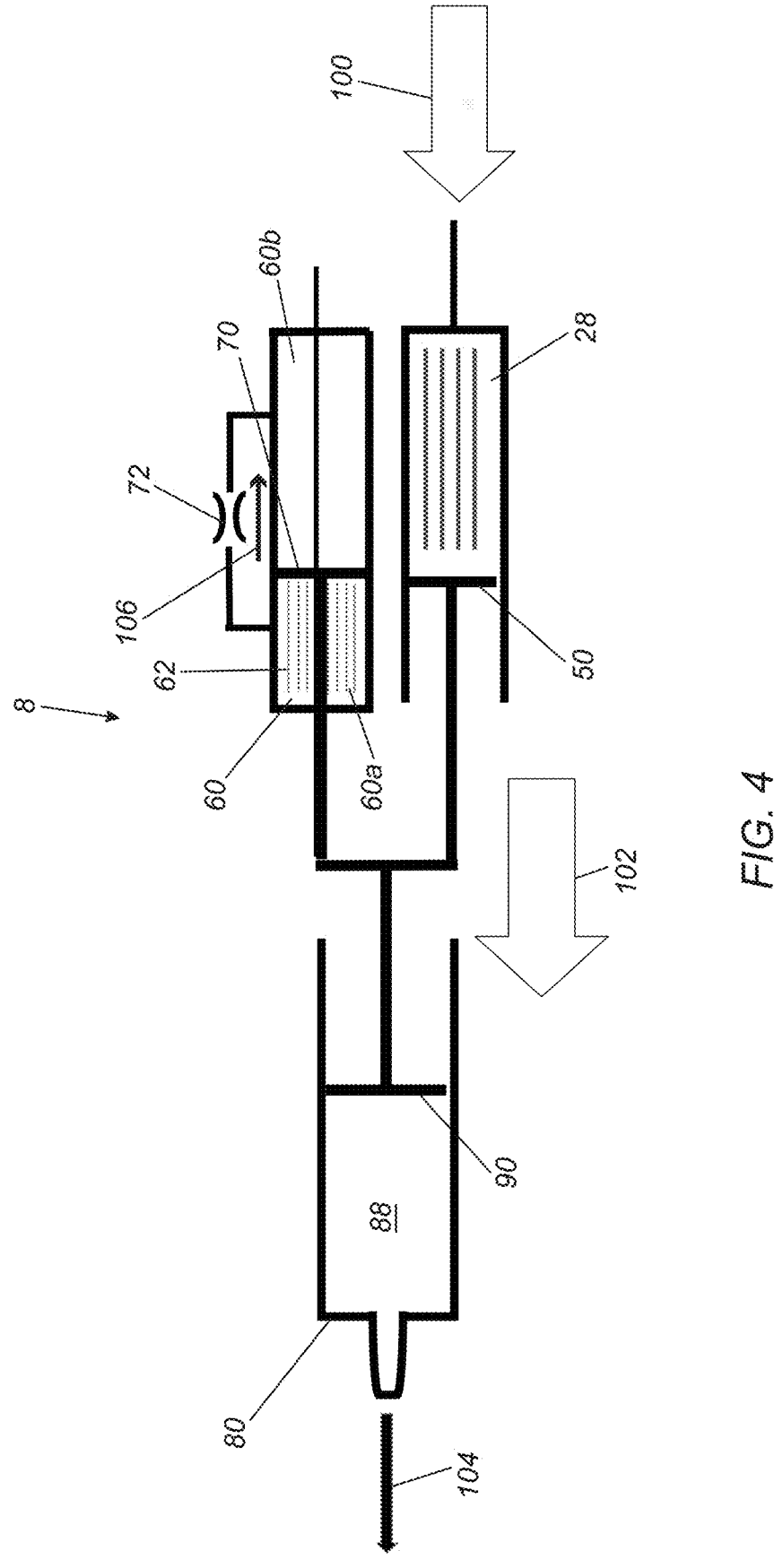
FIG. 4 is a schematic of the syringe driver of FIGS. 1A-1C.

As shown in FIGS. 3 and 4 and described elsewhere herein, when gas is delivered from the external air source into the gas chamber 28, as represented by arrow 100, the drive piston 50 moves from an initial proximal position (e.g., as shown in FIG. 3) distally towards a distal position (not shown), e.g., to the left as represented by arrow 102, thereby advancing the plunger 56 distally to deliver the agent from the syringe 80, as represented by arrow 104.

Returning to FIGS. 2A and 2B, in the example shown, the proximal end 52 of the drive piston 50 includes an outer O-ring 53 that is slidable along the inner wall 29 of the gas chamber 28, e.g., to provide a substantially airtight seal. Thus, pressurized gas introduced into the gas chamber 28 from the external air source may generate a pressure within the gas chamber 28 that applies a distal force to the proximal end 52 of the drive piston 50. In addition, as the driver piston 50 advances distally, the O-ring 53 may slide along the inner wall 29 and the distal end 54 of the driver piston, thereby guiding the drive piston 50 as it advances, e.g., alone or in combination with the passage 43 through the internal partition 42. Optionally, the housing 20 may include one or more additional partitions or supports, e.g., internal support 44 that may further support and/or guide the drive piston 50.

The syringe driver 10 also includes a damping mechanism, e.g., configured to provide an upper limit to the speed at which the driver piston 50 advances from the proximal position when the air source is actuated. For example, a damping fluid chamber 60 may be provided within the housing 20 that includes a damper piston 70 therein that are operatively coupled to the drive piston 50 to limit flow of a damping fluid within the damping fluid chamber 60 to provide a resistance to advancement of the drive piston 50.

For example, as shown in FIGS. 2A and 2B, the damping fluid chamber 60 is located within the drive piston 50, e.g., adjacent the proximal end 52, with the distal end 54 of the drive piston 50 extending distally from the damping fluid chamber 60. The damper piston 60 is provided within at an intermediate location within the damping fluid chamber 50, thereby separating the damping fluid chamber 60 into a first region 60a and a second region 60b. As shown in FIGS. 3 and 4, the first region 60a may initially contain a damping fluid 62, e.g., filled with an incompressible oil or other liquid having a viscosity substantially higher than the viscosity of the agent within the syringe 80, e.g., having a viscosity between about ten and one hundred thousand centipoise (10-100,000 cP).

As best seen in FIG. 3A, the damper piston 70 includes one or more orifices or other passages 72 extending therethrough, e.g., communicating between the first and second regions 60a, 60b of the damping fluid chamber 60, to allow the damping fluid 62 to flow between the regions 60a, 60b. The damper piston 70 may be axially fixed relative to the damping fluid chamber 60, e.g., such that the damper piston 70 remains substantially stationary as the drive piston 50 and, consequently, the damping fluid chamber 60, advances, e.g., during delivery of the agent. Alternatively, it will be appreciated that the damping mechanism may be reversed, e.g., such that the damper piston 70 moves with the driver piston 50 while the damping fluid chamber 60 remains stationary (not shown).

Consequently, axial movement of one of the damping fluid chamber 60 and damper piston relative to one another causes the damping fluid 62 to flow between the first and second regions 60a, 60b, e.g., as represented by arrows 106 in FIG. 3A. For example, as shown in FIGS. 3 and 4, distal movement of the drive piston 50, e.g., from the proximal position shown, causes the damping fluid chamber 60 to move distally, while the damper piston 70 remains stationary. This relative movement reduces the volume of the first chamber 60a, thereby generating a pressure that forces the damping fluid 62 to flow through the passage(s) 72 from the first region 60a into the second region 60b. Given the relatively high viscosity of the damping fluid 62 and the relatively small cross-section of the passage(s) 72, flow of the damping fluid may be limited, thereby limiting the speed of axial movement of the drive piston 50, as described further elsewhere herein.

As shown in FIGS. 2A and 2B, the damper piston 70 may be mounted on a shaft 74 including a proximal or first end 76 fixed relative to the plug 32 on the housing 20 and a distal or second end 78 located distal to the damping fluid chamber 60. The damping fluid chamber 60 may include one or more seals, e.g., O-rings 66, to accommodate the shaft 74 passing through the damping fluid chamber 60 and allowing relative axial movement, while providing a fluid tight to prevent the damping fluid 62 from leaking from the damping fluid chamber 60. Thus, when the drive piston 50, and consequently the damping fluid chamber 60, move distally, the shaft 74, and consequently the damper piston 70, remain stationary relative to the housing 20.

It will be appreciated that one or more parameters of the damping mechanism may be modified to provide a desired resistance to limit the speed of axial movement of the driver piston 50. For example, one or more of a) the viscosity of the damping fluid, b) the number and/or cross-sectional orifice size of the passage(s) 72, c) the diameter or other cross-section of the damping fluid chamber 60, and d) the diameter or other cross-section of the driver piston 50 may be modified as desired to adjust the maximum volumetric flowrate of the agent delivered from the syringe 80, e.g., for a given air pressure from the external air source.

Optionally, other damping arrangements may be provided. For example, the one or more passages may be provided in walls of the drive piston 50 and/or other structure within the housing 20 (not shown), i.e., to provide a narrow path between the first and second regions 60a, 60b. Alternatively, instead of providing one or more orifices or passages 72 in the damper piston 70, a valve (not shown) may be provided that communicates between the first and second regions 60a, 60b, e.g., within the damper piston 70 and/or other component within the housing 20, e.g., a pressure relief valve, a spring-loaded disk, a spring-loaded ball valve, and the like, to limit flow of the damping fluid 62 between the first and second regions 60a, 60b of the damping fluid chamber 60 in a desired manner.

Figure 5:
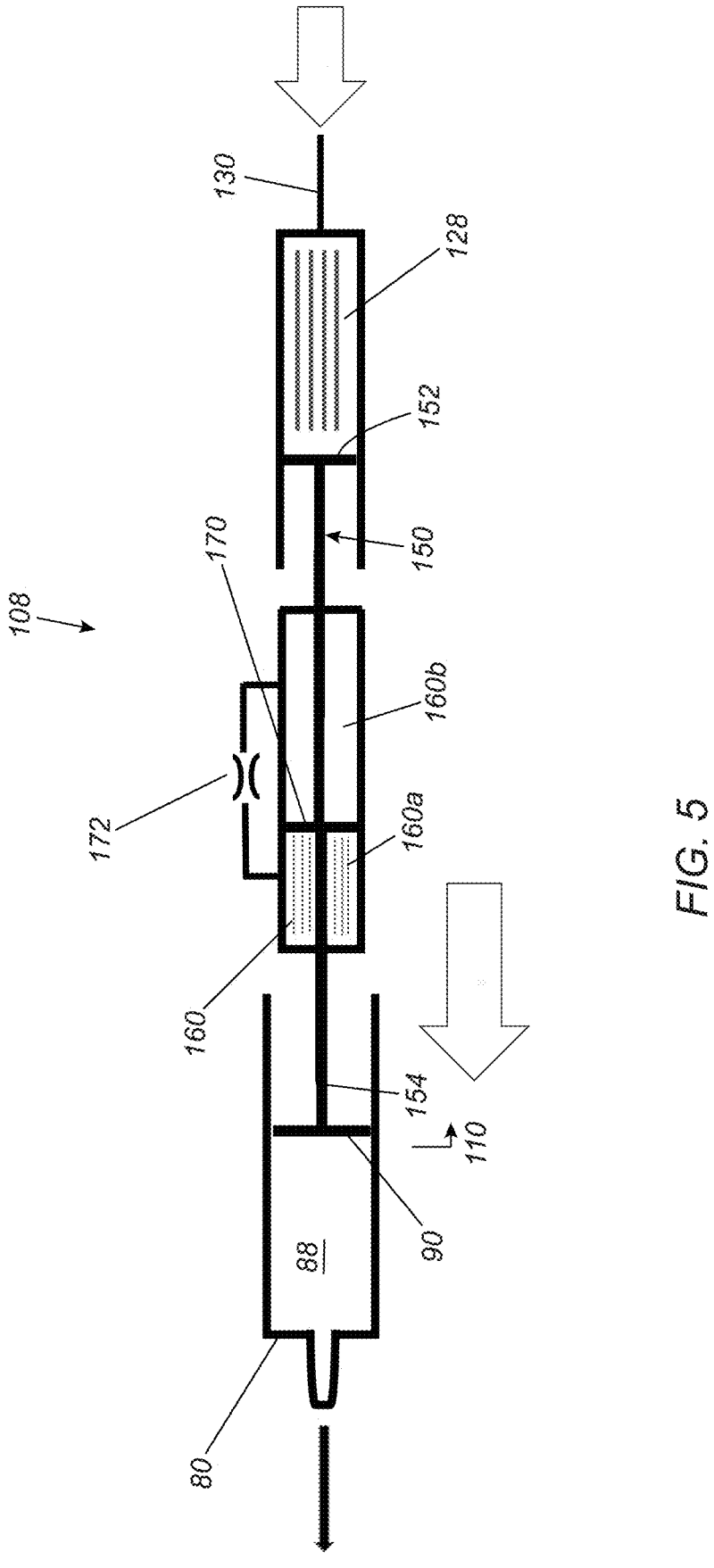
FIG. 5 is a schematic of an alternative example of a syringe driver.

In addition or alternatively, the damping mechanism may be provided in parallel or inline with the driver piston and the syringe piston, as desired. For example, turning to FIG. 5, an alternative arrangement is shown in which the damper mechanism is provided inline between a drive piston 150 and a syringe piston 90. As shown, a syringe driver 110 is provided that includes an air chamber 128 that may be connected to an external air source (not shown), e.g., via a port 130, to apply a distal force to the proximal end 152 of the driver piston 150, similar to the injector device 8. The distal end 154 of the driver piston 150 is coupled to the syringe piston 90 of syringe 80 such that distal movement of the drive piston 150 causes corresponding distal movement of the syringe piston 90 to deliver the agent within the interior 88 of the syringe 80, also similar to the injector device 8.

Unlike the syringe driver 10, the syringe driver 110 includes a damping fluid chamber 160 that is substantially stationary relative to the driver housing and, consequently, relative to the drive piston 150. For example, a damping fluid chamber may be mounted in or formed from surfaces of the housing. A damper piston 170 is provided within the damping fluid chamber 160, e.g., separating the damping fluid chamber 160 into first and second regions 160a, 160b, that is coupled directly to the drive piston 150. One or more orifices or pressure relief valves 172 are provided, e.g., in the damper piston 170, the drive piston 150, and/or otherwise within the housing 1120, to allow damping fluid within the first region 160a to flow therethrough into the second region 160b.

Thus, unlike the syringe driver 10, with this syringe driver 110, distal movement of the drive piston 150 causes corresponding distal movement to the damper piston 170, thereby pressurizing the damping fluid within the first region 160a and causing the damping fluid to flow through the passage(s) 172 into the second region 160b, thereby limiting flow of the agent, similar to the syringe driver 10.

With reference to FIGS. 3 and 4, an exemplary method for using the injector device 8, e.g., for performing an injection into a patient's eye or other target location, will now be described. Initially, a syringe 80 containing one or more agents may be inserted into the cavity 40 of the housing 20 such that the agent piston 90 of the syringe 80 is coupled to the distal end 54 of the drive piston 50. The outlet port 94 of the syringe 80 may be disposed adjacent the distal end 24 of the housing 20, e.g., including a Luer fitting or other connector extending from the distal end 24. A cannula may be connected to the outlet port 94, e.g., a needle or other elongate tubular member sized for introduction into the target location. For example, to deliver the agent into the posterior region of a patient's eye, a trocar or other tubular device may be positioned into the eye, e.g., using conventional methods, that is sized to receive the cannula connected to the outlet port 94.

An external air source, e.g., a surgical console, may be connected to the inlet gas port 30 on the syringe driver 10, which may be readied using conventional methods. The cannula on the outlet port 94 may be introduced into the patient's body, e.g., into the patient's eye through a trocar to position a tip of the cannula adjacent the posterior region.

Once the tip is positioned at the target location, the external air source may be activated to deliver pressurized gas into the port 30 and the gas chamber 28 to advance the drive piston from the initial proximal position towards the distal position, thereby advancing the plunger 56 and the agent piston 90 to deliver the agent from the syringe 80 into the target region. For example, a surgical console may include a foot pedal that the surgeon or other practitioner may actuate to increase the air pressure as desired to control the speed of advancement of the driver piston 50 and flow rate of the agent. However, because of the damping mechanism, movement of the drive piston between the proximal and distal positions causes the damping fluid to flow through the one or more passages 72 of the damper piston 70, i.e., from the first region 60a to the second region 60b of the damping fluid chamber 60, thereby limiting the velocity that the drive piston 50 advances, even if the surgeon applies excessive air pressure.

Movement of the driver piston 50 is opposed by the pressure in the damping fluid chamber 60 acting on the damper piston 70 resulting from the resistance of flow of the damping fluid 62 through the passage(s) 72 between the regions 60a, 60b. When the force balances between the air side (i.e., from the external air source pressure) and the damping fluid side (i.e., from the pressure generated in the damping fluid chamber 60), the velocity of the drive piston 50 and plunger 56 and, therefore the volumetric flowrate of the agent from the syringe 80 is at its maximum. Thus, the damping mechanism may provide the primary resistance to the flow of the agent being delivered, i.e., given the relatively high viscosity of the damping fluid relative to the other resistances involved in the injector device, agent, and/or patient's anatomy, resulting in a throttling action that provides an upper, safe limit to the flow rate of the agent and/or allowing for exquisite control of the delivery flow rate.

Further, in describing representative examples, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A syringe driver for use with an external air source, comprising:

a housing comprising a port communicating with a gas chamber within the housing and connectable to the external air source, and a cavity sized to receive a syringe containing an agent;

a drive piston comprising an elongate member including a first end slidably disposed within the gas chamber and a second end comprising a plunger connectable to the syringe received within the cavity, the drive piston movable from an initial first position to a second position when gas is delivered from the air source into the gas chamber to generate pressure within the gas chamber that applies a distal force to advance the first end of the drive piston within the gas chamber, thereby advancing the second end of the drive piston and the plunger to deliver the agent from the syringe; and a damping fluid chamber including a damper piston disposed therein between a first region of the damping fluid chamber filled with damping fluid and a second region of the damping fluid chamber, and one or more passages or valves communicating between the first region and the second region such that movement of the drive piston between the first and second positions causes the damping fluid to flow through the one or more passages or valves from the first region to the second region, thereby limiting movement of the drive piston, wherein the damping fluid chamber is located within an interior of the drive piston adjacent the first proximal end of the drive piston such that the damping fluid chamber moves with the drive piston as the drive piston moves from the first position to the second position to cause the damping fluid to flow between the first region and the second region.

2. The syringe driver of claim 1, wherein the damper piston is fixed relative to the housing within the interior of the drive piston and includes the one or more passages or valves such that, when the drive piston and damping fluid chamber move, the damper piston remains substantially stationary, thereby causing the damping fluid to flow through the damping piston between the first region and the second region.

3. The syringe driver of claim 2, wherein the damper piston is mounted on a shaft fixed relative to the housing.

4. The syringe driver of claim 1, wherein the damping fluid chamber is substantially stationary relative to the housing and wherein the damper piston is coupled to the drive piston such that the damper piston moves when the drive piston moves from the first position to the second position to cause the damping fluid to flow between the first region and the second region.

5. The syringe driver of claim 1, wherein the damping fluid has a viscosity that limits a flow rate through the one or more passages or valves to limit a speed at which the drive piston moves between the first and second positions.

6. A syringe driver for use with an external air source, comprising:

a housing comprising a proximal end including a port communicating with a gas chamber within the housing and connectable to the external air source, and a distal end including a cavity sized to receive a syringe containing an agent;

a drive piston comprising a first end slidably disposed within the gas chamber and a second end comprising a plunger connectable to the syringe received within the cavity, the drive piston movable from an initial proximal position to a distal position when gas is delivered from the air source into the gas chamber to generate pressure within the gas chamber that applies a distal force to advance the first end of the drive piston within the gas chamber, thereby advancing the second end of the drive piston and the plunger to deliver the agent from the syringe; and a damping fluid chamber including a damper piston disposed therein between a first region of the damping fluid chamber filled with damping fluid and a second region of the damping fluid chamber, and one or more passages or valves communicating between the first region and the second region such that movement of the drive piston between the proximal and distal positions causes the damping fluid to flow through the one or more passages or valves from the first region to the second region, thereby limiting movement of the drive piston, wherein the one or more passages or valves comprises one or more passages in the damper piston that communicate between the first and second regions.

7. The syringe driver of claim 6, wherein the damping fluid chamber is located within an interior of the drive piston such that the damping fluid chamber moves distally with the drive piston as the drive piston moves from the proximal position to the distal position to cause the damping fluid to flow between the first region and the second region.

8. The syringe driver of claim 7, wherein the damper piston is fixed relative to the housing such that, when the drive piston and damping fluid chamber move, the damper piston remains substantially stationary, thereby causing the damping fluid to flow between the first region and the second region.

9. The syringe driver of claim 8, wherein the one or more passages or valves are located within the drive piston and communicate between the first and second regions.

10. The syringe driver of claim 6, wherein the distal end of the drive piston extends distally from the damping fluid chamber into the cavity.

11. The syringe driver of claim 6, wherein the damping fluid chamber is substantially stationary relative to the housing and wherein the damper piston is coupled to the drive piston such that the damper piston moves distally when the drive piston moves from the proximal position to the distal position to cause the damping fluid to flow between the first region and the second region.

12. The syringe driver of claim 11, wherein the damper piston is mounted on the drive piston between the first end of the drive piston and the second end.

13. The syringe driver of claim 12, wherein the damping fluid chamber is located between the gas chamber and the cavity within the housing.

14. The syringe driver of claim 6, wherein the damping fluid has a viscosity that limits a flow rate through the one or more passages or valves to limit a speed at which the drive piston moves between the proximal and distal positions.

15. The syringe driver of claim 7, wherein the one or more passages or valves comprises a valve limiting flow between the first and second regions.

16. The syringe driver of claim 15, wherein the one or more passages or valves comprises one of a pressure relief valve, a spring-loaded ball valve, and a spring-loaded disk.

17. An injector device for use with an external air source, comprising:

a housing comprising a proximal end including a port communicating with a gas chamber within the housing and connectable to the external air source, and a distal end;

an agent chamber within the distal end including an agent piston and an outlet port extending from the distal end;

a drive piston comprising a first end slidably disposed within the gas chamber and a second end comprising a plunger connected to the agent piston, the drive piston movable from an initial proximal position to a distal position when gas is delivered from the air source into the gas chamber to generate pressure within the gas chamber that applies a distal force to advance the first end of the drive piston within the gas chamber, thereby advancing the second end of the drive piston, the plunger, and the agent piston to deliver the agent from the from the agent chamber through the outlet port; and a damping fluid chamber including a damper piston disposed therein between a first region of the damping fluid chamber filled with damping fluid and a second region of the damping fluid chamber, and one or more passages or valves communicating between the first region and the second region such that movement of the drive piston between the proximal and distal positions causes the damping fluid to flow through the one or more passages or valves from the first region to the second region, thereby limiting movement of the drive piston, wherein the damping fluid chamber is located within the drive piston such that the damping fluid chamber moves distally with the drive piston as the drive piston moves from the proximal position to the distal position to cause the damping fluid to flow between the first region and the second region.

18. The injector device of claim 17, wherein:

the damping fluid chamber is located within the drive piston adjacent the proximal end;

the damping piston is provided at an intermediate location within the damping fluid chamber, thereby dividing the damping fluid chamber into the first and second regions;

the one or more passages or valves comprise one or more passages extending through the damping piston that communicate between the first and second regions; and the damping piston is fixed relative to the housing such that, when the drive piston moves between the proximal and distal positions, the damper piston remains substantially stationary, thereby causing the damping fluid to flow through the one or more passages between the first region and the second region.

19. The injector device of claim 17, wherein:

the damping fluid chamber is located within the drive piston adjacent the proximal end;

the damping piston is provided at an intermediate location within the damping fluid chamber, thereby dividing the damping fluid chamber into the first and second regions;

the one or more passages or valves comprising one or more passages within an interior wall of the drive piston that communicate between the first and second regions; and the damping piston is fixed relative to the housing such that when the drive piston moves between the proximal and distal positions, the damper piston remains substantially stationary, thereby causing the damping fluid to flow through the one or more passages between the first region and the second region.

20. The injector device of claim 17, further comprising a source of compressible gas connected to the port as the external air source, the source of compressible gas configured to be activated to deliver pressurized gas into the port and the gas chamber to advance the drive piston from the proximal position towards the distal position, thereby advancing the plunger and the agent piston to deliver the agent from the syringe.

21. The injector device of claim 20, wherein the source of compressible gas comprises an actuator configured to be actuated to increase the gas pressure to control the speed of advancement of the driver piston and flow rate of the agent while movement of the drive piston between the proximal and distal positions causes the damping fluid to flow through the one or more passages or valves from the first region to the second region, thereby limiting a velocity that the drive piston advances.

22. The injector device of claim 21, wherein the actuator comprises a foot pedal.

23. The injector device of claim 17, wherein the housing comprises a cavity adjacent the distal end, the injector device further comprising a syringe received within the cavity that includes the agent chamber, the agent piston, and the outlet port.

24. The injector device of claim 23, wherein the housing and the syringe comprise one or more connectors for securing the syringe within the cavity.

* * * * *